United States Patent [19]
Li

[11] Patent Number: 6,149,669
[45] Date of Patent: *Nov. 21, 2000

[54] SURGICAL FASTENER ASSEMBLY METHOD OF USE

[75] Inventor: Lehmann K. Li, Milford, Conn.

[73] Assignee: Li Medical Technologies, Inc., Shelton, Conn.

[*] Notice: This patent issued on a continued prosecution application filed under 37 CFR 1.53(d), and is subject to the twenty year patent term provisions of 35 U.S.C. 154(a)(2).

[21] Appl. No.: 08/961,511

[22] Filed: Oct. 30, 1997

[51] Int. Cl.⁷ .................................................... A61B 17/04
[52] U.S. Cl. .............................. 606/232; 606/63; 606/68; 606/72
[58] Field of Search .................................. 623/13, 13.14, 623/13.17, 13.11; 606/63, 64, 65, 72, 75, 68, 232, 233

[56] References Cited

U.S. PATENT DOCUMENTS

| | | | |
|---|---|---|---|
| 4,007,743 | 2/1977 | Blake | 606/232 |
| 4,409,974 | 10/1983 | Freedland | 606/232 |
| 4,532,926 | 8/1985 | O'Holla | 606/232 |
| 4,632,101 | 12/1986 | Freedland | 606/68 |
| 5,366,480 | 11/1994 | Corriveau et al. | |
| 5,370,661 | 12/1994 | Branch | |
| 5,527,341 | 6/1996 | Goglewski et al. | |
| 5,545,180 | 8/1996 | Le et al. | 606/232 |
| 5,569,306 | 10/1996 | Thal | 606/232 |
| 5,575,819 | 11/1996 | Amis | 623/13 |
| 5,630,824 | 5/1997 | Hart | |
| 5,643,321 | 7/1997 | McDevitt | 606/232 |
| 5,645,589 | 7/1997 | Li | 623/16 |
| 5,658,313 | 8/1997 | Thal | |
| 5,690,678 | 11/1997 | Johnson | |
| 5,741,282 | 4/1998 | Anspach, III et al. | 606/151 |
| 5,810,820 | 9/1998 | Santori et al. | 606/63 |
| 5,891,168 | 4/1999 | Thal | 606/232 |
| 5,893,850 | 4/1999 | Cachia | 606/63 |

*Primary Examiner*—Paul B. Prebilic
*Attorney, Agent, or Firm*—Ostrolenk, Faber, Gerb & Soffen, LLP

[57] ABSTRACT

A surgical fastener method for fastening a first bio-organic tissue member to a second bio-organic tissue member comprising a plurality of suture anchors for insertion through respective openings in the first tissue member into respective aligned boreholes in the second tissue member and for securement in the borehole, a suture coupled to each of the plurality of suture anchors and fastening the plurality of suture anchors together, the suture fastening the plurality of suture anchors together being adapted to extend, in use, from a respective suture anchor through the respective opening in the first tissue member and spanning between respective suture anchors across a proximal surface of the first member with a preset tension thereby to secure the first member to the second member.

35 Claims, 11 Drawing Sheets

SURGICAL FASTENER ASSEMBLY METHOD OF USE

BACKGROUND OF THE INVENTION

The present invention relates to surgical fasteners and anchors, and in particular, to a surgical fastener assembly for securing two or more tissue members together. The present invention is related to applicant's co-pending applications Ser. No. 08/294,067, filed Aug. 22, 1994 entitled Anchor and Method for Securement into a Bore and Ser. No. 08/426,715, filed Apr. 21, 1995 entitled Fixation Device and Method for Installing Same.

The present invention comprises a surgical fastener assembly employing suture anchors of the type disclosed in the above-identified co-pending applications which is particularly useful for suturing two or more tissue members together, for example, ligaments or muscles to bone. In particular, the present invention provides a surgical fastener assembly which eliminates the need for the surgeon to have to thread sutures.

In the past, when applying suture anchors, an anchor having a suture attached thereto is installed into a borehole, typically formed in bone. The suture can then be used to suture a muscle or ligament to the bone, for example, the rotator cuff ligament of the shoulder. With reference to FIG. 7, which generically shows a prior art suture anchor by the reference numeral 10, a borehole 12 is drilled into the bone 14. The suture anchor 10, with suture 16 attached, is then installed into the borehole 12. In the illustration depicted in FIG. 7, the aim is to secure the ligament 18 to the bone 14. The ligament 18 might be, for example, the rotator cuff, which comprises a thin slab. The suture anchors 10 are inserted into the boreholes 12. The extending free ends of the sutures 16 are then threaded, with surgical needles 17, through the ligament 18 and tied together, as shown at 16A, to secure the ligament 18 in place on the bone 14.

This is a cumbersome process because the surgeon must threaded and manipulate the fine sutures in the surgical area despite swelling, bleeding, the presence of other tissue, etc.

SUMMARY OF THE INVENTION

It is, accordingly, an object of the present invention to provide a surgical fastener assembly which eliminates the need for the surgeon to have to thread sutures to secure tissues together.

Yet still another object of the present invention is to employ a suture anchor of the type described in applicant's above-identified co-pending patent applications in a surgical fastener assembly.

Yet still a further object of the present invention is to provide a surgical fastener assembly comprising an individual suture anchor or a plurality of suture anchors coupled together by sutures which eliminates the need to have to thread the sutures and causes the fixation of a first tissue to a second tissue by the operation of inserting the suture anchor or plurality of suture anchors through the first tissue to be secured into respective boreholes in the second tissue.

A further object of the invention is to provide a method for fastening a first tissue member to a second tissue member without the need to thread sutures.

The above and other objects of the present invention are achieved by a surgical fastener assembly for fastening a first bio-organic tissue member to a second bio-organic tissue member comprising, a plurality of suture anchors for insertion through respective openings in the first tissue member into respective aligned boreholes in the second tissue member and for securement in the respective borehole, a suture coupled to each of the plurality of suture anchors and fastening the plurality of suture anchors together, the suture fastening the plurality of suture anchors together being adapted to extend, in use, from a respective suture anchor through a respective opening in the first tissue member and spanning between respective suture anchors across a proximal surface of the first member with a preset tension thereby to secure the first member to the second member.

The above and other objects of the present invention are also achieved by a surgical fastener assembly for fastening a first bio-organic tissue member to a second bio-organic tissue member comprising an anchor for insertion through an opening in the first member into an aligned borehole in the second member and for securement in the borehole, the anchor having an engaging portion and a longitudinal direction defined by a longitudinal axis alignable with the axis of the borehole, an extending member disposed about the anchor axis proximally with respect to the engaging portion and having a pivotal connection to the anchor, the extending member having an extent greater than the diameter of the borehole, the anchor being securable in the borehole with the extending member overlying a proximal surface of the first member and with a preset tension in the pivotal connection between the extending member and the anchor to secure the first member to the second member between the extending member and the second member.

The above and other objects of the present invention are furthermore achieved by a method for fastening a first bio-organic tissue member to a second bio-organic tissue member comprising forming a first opening in the first tissue member and an aligned first borehole in the second tissue member, inserting a first suture anchor coupled by a suture to a second suture anchor, through the first opening in the first member into the aligned borehole in the second member and securing the first suture anchor in the borehole, the suture attached to the first suture anchor thereby passing out of the borehole through the first hole in the first member, forming a second hole in the first member and an aligned second borehole in the second member, inserting the second suture anchor through the second opening in the first member into the second borehole in the second member and securing the second suture anchor in the second borehole with a preset tension in the suture connecting the first and second suture anchors together, the suture spanning across a proximal surface of the first member thereby to hold the first member securely to the second member The above and other objects of the present invention are also achieved by a method for fastening a first bio-organic tissue member to a second bio-organic tissue member comprising the steps of forming a first opening in the first member and an aligned first borehole in the second member, inserting an anchor through the first opening in the first member into the aligned first borehole in the second member and securing the anchor in the first borehole with an engaging portion of the anchor, the anchor pivotally connected to an extending member disposed about an axis of the anchor proximally with respect to the engaging portion, the extending member have an extent greater than the diameter of the first borehole and overlying a portion of a proximal surface of the first member surrounding the first opening; and securing the anchor in the first borehole with the extending member overlying the proximal surface of the first member with a preset tension in the pivotal connection between the extending member and the anchor to secure the first member to the second member between the extending member and the second member.

Other objects, features and advantages of the present invention will become apparent from the detailed description which follows.

BRIEF DESCRIPTION OF THE DRAWINGS

The invention will now be described in greater detail in the following detailed description with reference to the drawings in which.

DETAILED DESCRIPTION OF EMBODIMENTS OF THE INVENTION

Figure 1:
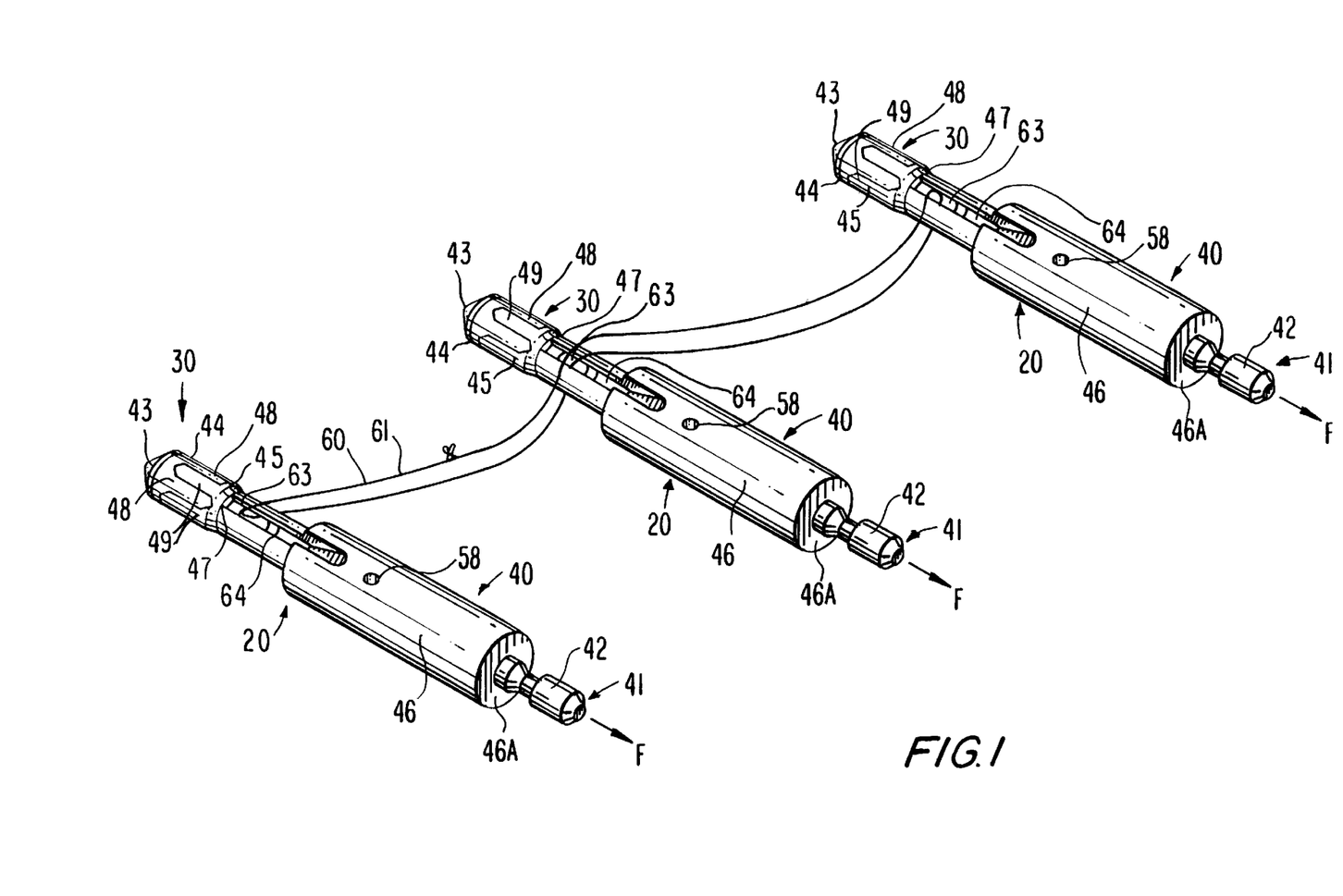
FIG. 1 shows in a perspective view a surgical fastener assembly according to the present invention comprising a plurality of individual unactuated suture anchors coupled together by sutures.
Figure 1A:
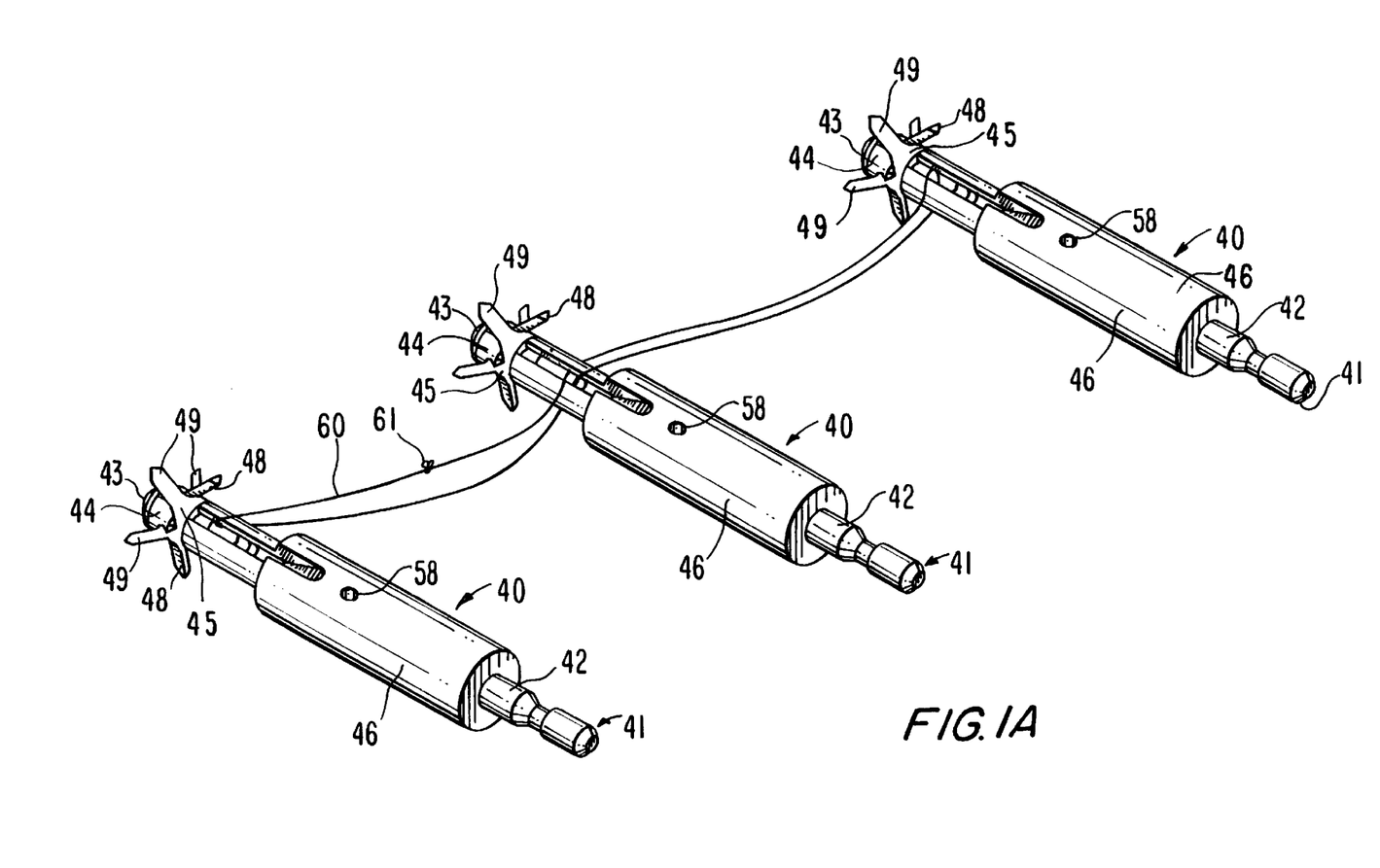
FIG. 1A shows in a perspective view the surgical fastener assembly of FIG. 1 showing the individual suture anchors in their actuated position, as they would be once installed in a borehole in tissue, but prior to the release of a disposable portion of the suture anchors.
Figure 2:
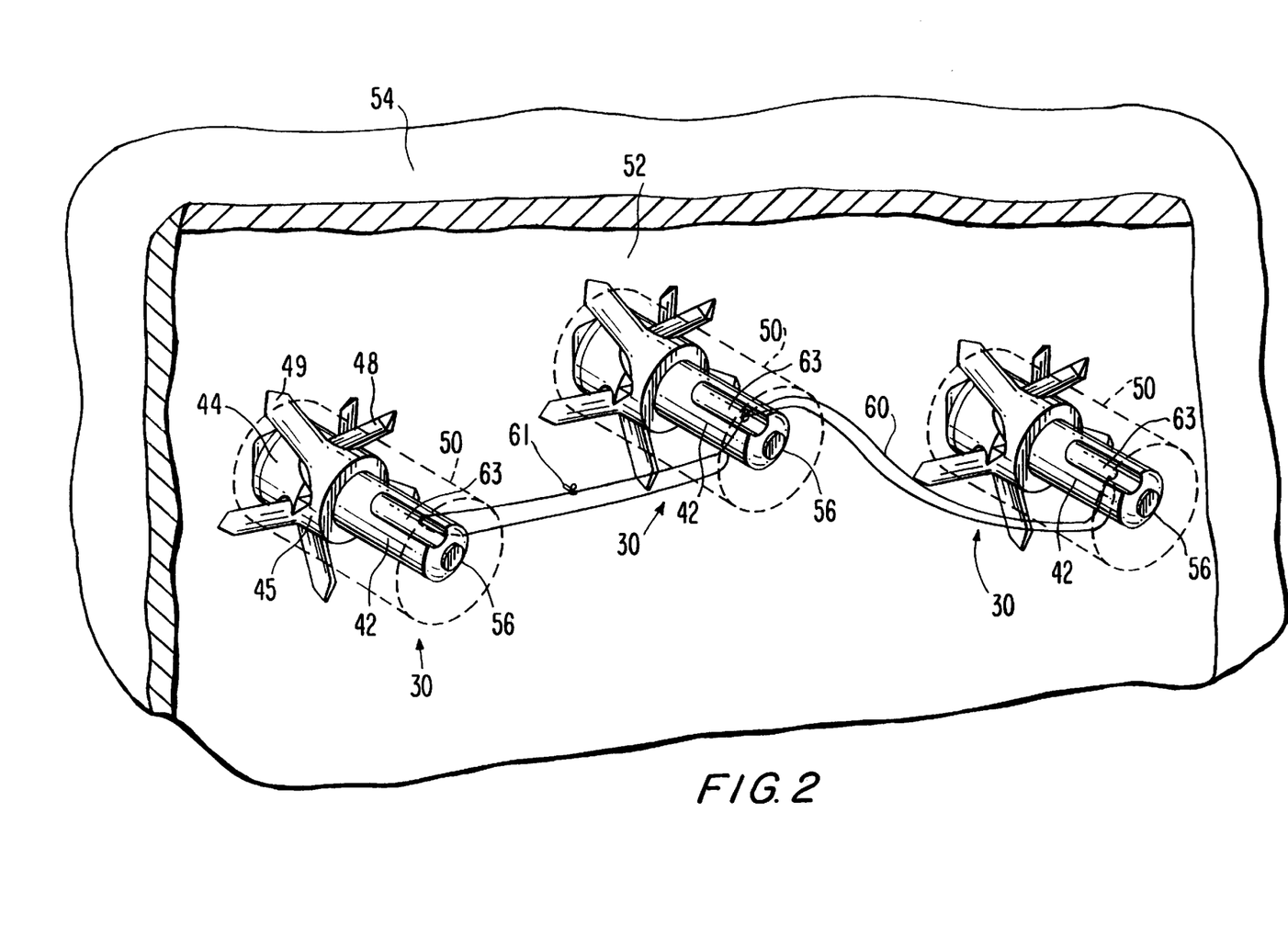
FIG. 2 shows in a perspective view the surgical fastener assembly of FIGS. 1 and 1A inserted in boreholes in a tissue member securing another tissue member to the first mentioned tissue member, the individual suture anchors being shown after a disposable portion of the suture anchors have released from the portion shown secured in the tissue.

With reference now to the drawings, FIGS. 1, 1A and 2 show a first embodiment of the surgical fastener assembly according to the present invention. In the embodiment shown in FIGS. 1, 1A and 2, the surgical fastener assembly comprises a plurality of individual suture anchors 20 of the type described in applicant's above-identified co-pending patent applications. The individual suture anchors 20 are tied together by a suture or sutures 60. In the example shown in FIG. 1, a single suture 60 is threaded through a plurality, in this case three, suture anchors 20 and tied together. However, individual sutures 60, appropriately tied together and to the individual suture anchors 20 can also be used.

The individual suture anchors of the type shown in FIG. 1 are identified generally by reference numeral 20. Each suture anchor 20 comprises two connected portions, a portion 30 to be secured into tissue and a disposable portion 40. The portion 30 (See FIG. 2) is the portion of the suture anchor which is inserted and fastened into tissue. The portion 40 is adapted to be grasped by an installation tool, not shown, at the end 41, is releasable from the portion 30, and after use, is disposed of. The installation tool (not shown) exerts a force in the direction of the arrow F, pulling a shaft 42 at the proximal end, which shaft extends longitudinally through the suture anchor 20 and is provided with an enlarged head 43 at the distal end. In the embodiment shown in FIG. 1, two sections 44 and 45 of the portion 30 are disposed concentrically distally about the shaft 42. Shaft 42 extends longitudinally through a proximal cylindrical member 46. The member 46 terminates at a distal end thereof at a surface 47 in abutting relationship with the member 45 and at a proximal end at a surface 46A.

In the embodiment shown in FIG. 1, the members 44 and 45 include, respectively, a plurality of interdigitated longitudinally extending fingers 48 and 49. When shaft 42 is pulled in the direction of arrow F with the cylindrical member 46 being held stationary by proximal surface 46A against the installation tool, enlarged end 43 of the shaft 42 exerts a force on the member 44 causing the members 44 and 45 to move longitudinally relatively toward each other. The ends of the fingers 48 and 49 abut against cam surfaces disposed on respective opposite members 45 and 44 between the fingers. As the fingers 48 and 49 move relatively longitudinally, the fingers 48 and 49 move radially outwardly, as best shown in FIG. 2, due to the cam surfaces engaging with the under surface of the fingers. The fingers thus penetrate into the sidewall of a borehole into which the suture anchor is inserted. FIG. 1A shows the suture anchors in their entirety in the actuated position, but before the disposable portion 40 has been released.

Once the fingers 48 and 49 of each suture anchor have penetrated into the side wall of the borehole to their maximum extent, the shaft 42 is caused to snap at a specified location of reduced strength 56 by a preset amount of force F so as to separate the portion 40 comprising member 46 and a disposable portion of the shaft 42 therein from the portion 30 of the suture anchor which remains embedded in the borehole. The amount of force needed to snap the shaft 42 at frangible location 56 is greater than the maximum force needed to set the fingers into their actuated, penetrating position into the bone tissue.

FIG. 2 shows the portion 30 of each suture anchor in its actuated position with the fingers embedded in a borehole 50 in bone tissue 54 and securing ligament. 52 to bone 54. As shown in FIG. 2, an area of reduced thickness 56 of the shaft 42 is provided so that the shaft 42 snaps upon the application of a predetermined tensile force in the shaft 42.

The cylinder member 46 containing the portion of the shaft 42 that has snapped away from the portion of the shaft 42 that remains embedded in the bore is then disposed of. The disposable portion of shaft 42 remains secured to the cylindrical member 46 by alignment pin 58 which is received with an elongated slot or channel in the shaft 42. Accordingly, the shaft 42 also cannot rotate with respect to the cylindrical member 46. This is necessary to prevent the suture 60 from being caught between the member 46 and the shaft 42 at the location where the suture is threaded through a hole 63 in shaft 42.

The suture shown in FIGS. 1, 1A and 2 may comprise a single loop of suture 60 tied together by a knot 61 which is looped through an opening 63 provided in each shaft 42. A channel 64 is provided in the cylindrical member 46 through which the suture 60 extends during installation to keep the suture in a non-interfering position. A channel is also provided on the opposite side of the member 46, which cannot be seen in FIG. 1. Accordingly, each of the individual suture anchors 20 is coupled together by a suture.

Although the embodiment shown uses a single loop of suture to connect the plurality of suture anchors together, individual segments of suture, appropriately tied together, can also be used. The plurality of suture anchors must all be connected together by portions of sutures. Although FIG. 1 shows three individual suture anchors, any number of suture anchors can be used. Accordingly, in the embodiment of the invention shown in FIG. 1, as few as two suture anchors coupled together can be used. There is no upper limit to the number of suture anchors which can be coupled together, although in practice, it is likely that the number will be a limited number determined by the size of the suturing operation required.

FIG. 2 shows the individual suture anchors after they have been inserted through an opening in the ligament 52 into an aligned borehole 50 in the bone 54 and showing the sutures spanning the individual suture anchors to maintain the ligament 52 secured to the bone 54.

Figure 5:
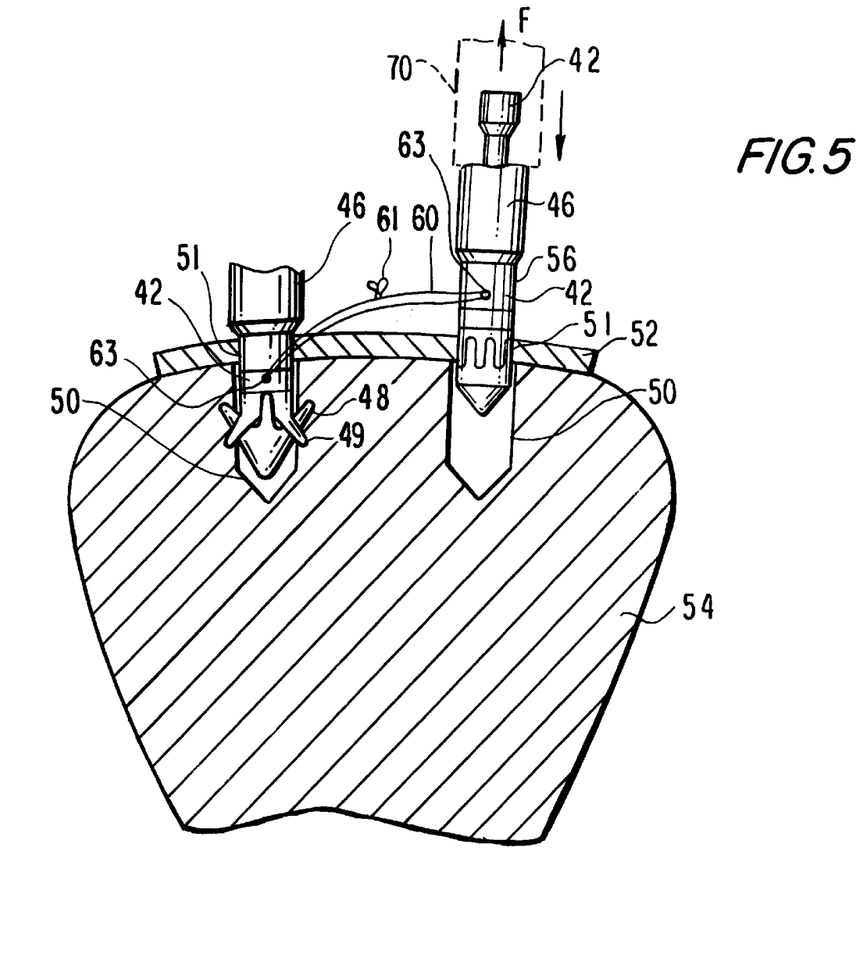
FIG. 5 shows in a side view, the surgical fastener assembly of the invention comprising a plurality of suture anchors coupled together by a suture and holding a first tissue member to a second tissue member, one of the suture anchors being shown in its actuated position prior to removal of the disposable portion of the suture anchor and the other suture anchor being shown during the step of insertion.

FIG. 5 shows a side view of the suture anchor assembly according to the present invention in a schematic view. As illustrated, a borehole 50 is drilled or otherwise provided in the tissue member 54, e.g., bone tissue. Preferably, at the same time, in one operation, an opening 51 is made in the tissue member 52, e.g. a ligament. One of the suture anchors coupled together by sutures 60 is individually inserted into the installation tool shown partly in FIG. 5 by the dotted lines 70. The suture anchor is then inserted through the opening 51 in tissue 52 and then into borehole 50 in tissue 54 to the desired depth. The installation tool exerts force F on the shaft 42 causing the members 44 and 45 to move relatively toward each other forcing the longitudinally directed fingers 48 and 49 outwardly into the side walls of the borehole to thus secure the anchor to the bone. Preferably the fingers 48 and 49 are sharpened to aid in penetration. With increased actuation of the installation tool, the tensile force in shaft 42 increases beyond the preset force required to snap shaft 42 at frangible connection 56, thus releasing portion 40 from the suture anchor 20 and leaving only portion 30, with suture attached, installed in borehole 50. The suture 60 connecting the anchor to the remaining individual suture anchors then extends out of the borehole 50, through the opening in the ligament 51. Another suture anchor is then installed on the insertion tool and inserted into a respective borehole through the tissue 52. When the required tension in the suture 60 is achieved, the suture anchor is actuated and the fingers of the suture anchor are caused to penetrate into the sidewall of the borehole. Portion 40 is then caused to separate from the portion 30 of the suture anchor remaining in the borehole at the frangible connection 56. The tissue 52 is now held securely to the tissue 54 by the spanning action of the suture 60 between the two suture anchors. The process is repeated until all connected suture anchors are installed.

Figure 5A:
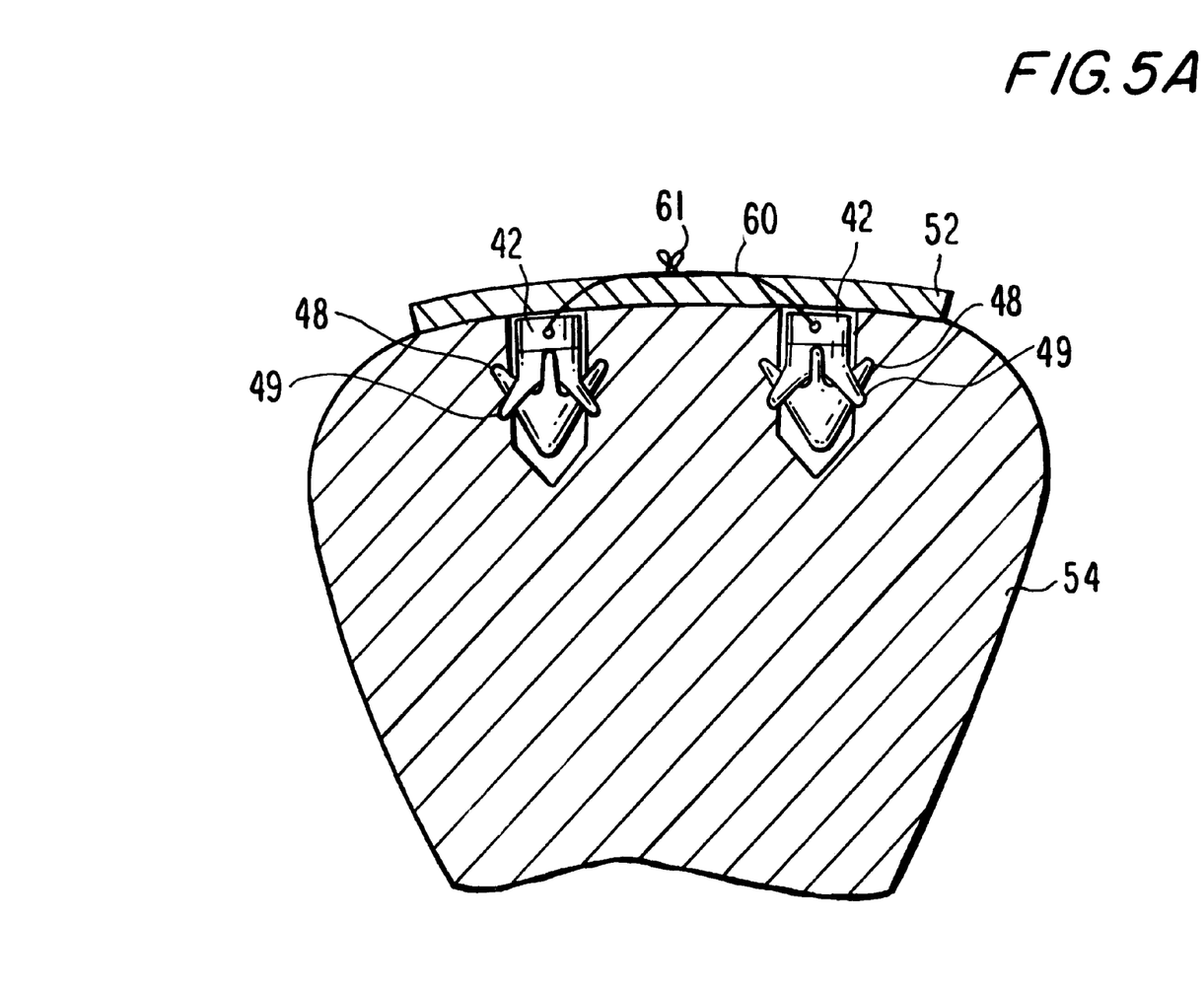
FIG. 5A shows the surgical fastener assembly of FIG. 5 after deployment and after the disposable portion of each of the suture anchors of the assembly has been removed.

FIG. 5A shows the suture anchors of the surgical fastener assembly in position after the shaft 42 has fractured at the portion 56, leaving the individual suture anchor portions 30 in position with the suture 60 spanning across the ligament 52 with the required tension to thereby secure the ligament 52 in position on the bone 54. As discussed, as many suture anchors as necessary to secure the tissue member together are employed.

Accordingly, prior to installation of the surgical fastener of the invention, the surgeon determines the make-up of the surgical fastener required, e.g., whether a fastener having, two, three, four, etc., suture anchors will be employed. According to the invention, surgical fasteners having various numbers of coupled suture anchors may be provided in advance. The surgeon selects the fastener having the appropriate number of suture anchors for the particular operation.

Although in the illustrations described a borehole 50 is pre-drilled in the bone 54, end 43 of the shaft 42 may have a pointed self-tapping head which is driven through tissue 52 into the tissue 54, thus forming the borehole 50 and opening 51 in the same operation as the installation of the anchor.

Figure 3:
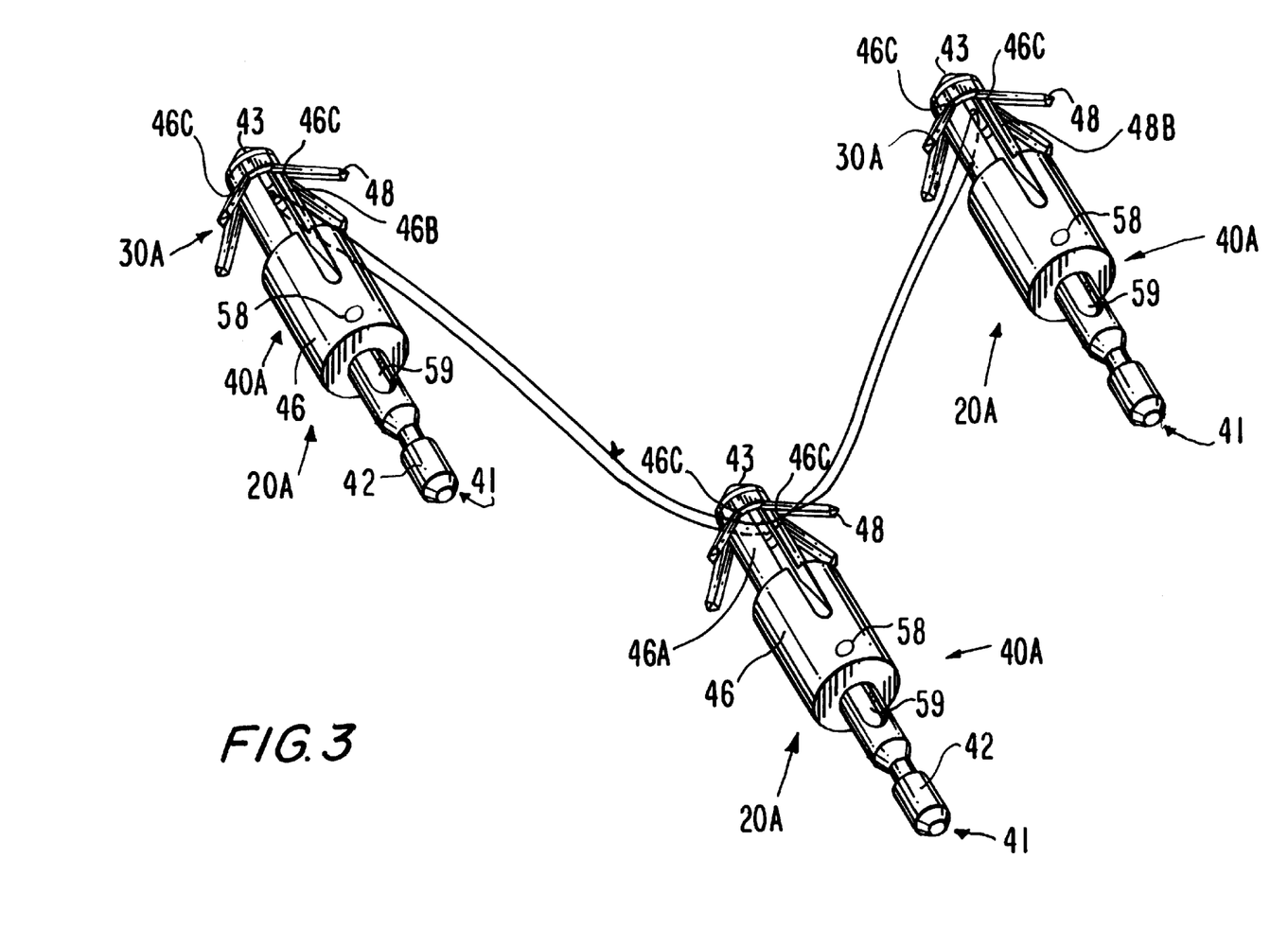
FIG. 3 shows in a perspective view a second embodiment of the present invention showing a surgical fastener assembly comprising a plurality of suture anchors coupled together by sutures.
Figure 4:
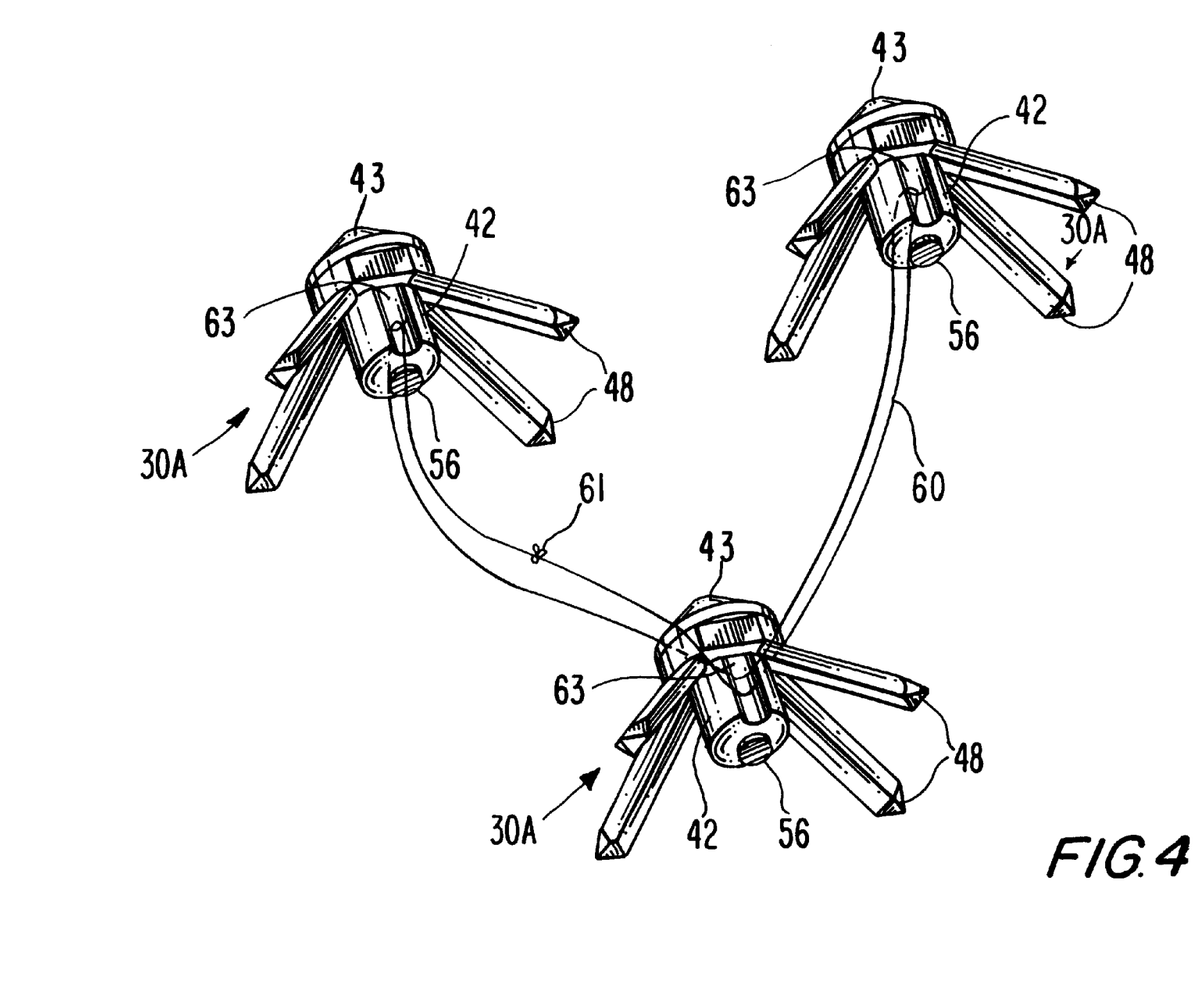
FIG. 4 shows in a perspective view the surgical fastener assembly of FIG. 3 after deployment.

FIG. 3 shows an alternative embodiment of the invention. This suture anchor 20A comprises a penetrating portion 30A and a disposable portion 40A. In the embodiment shown in FIG. 3, the suture anchor 20A includes only one set of longitudinally directed fingers 48 extending proximally on portion 30A. The fingers are caused to extend radially by engagement with respective cam surfaces 46C disposed on a portion 46B of reduced thickness of the cylindrical member 46. Otherwise, the embodiment shown in FIGS. 3 and 4 is substantially the same as the embodiment shown in FIGS. 1, 1A and 2 and like reference numerals have been applied to like elements. Not visible in FIGS. 1, 1A and 2 but visible in FIG. 3 is the alignment channel 59 which receives the alignment pin 58 to prevent the shaft 42 from turning with respect to the cylindrical member 46 and also keeping the shaft 42 from separating from the cylindrical member 46. In FIGS. 3 and 4, the longitudinally directed fingers are shown in their actuated position. In their unactuated position, not shown, the fingers 48 would be directed axially along the longitudinal direction of the suture anchor 20A. Also, FIGS. 3 and 4 show proximally directed fingers 48. It is also possible to provide fingers extending only distally, as desirable in certain. installations.

Figure 6A:
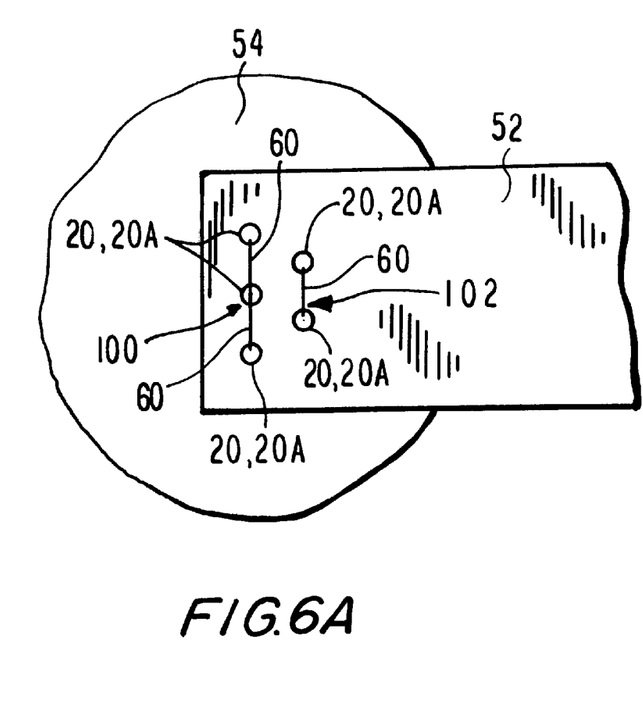
FIGS. 6A, 6B and 6C show, illustratively, in plan views, groups of suture anchors comprising surgical fastener assemblies according to the present invention employed to secure first and second tissue members together.
Figure 6B:
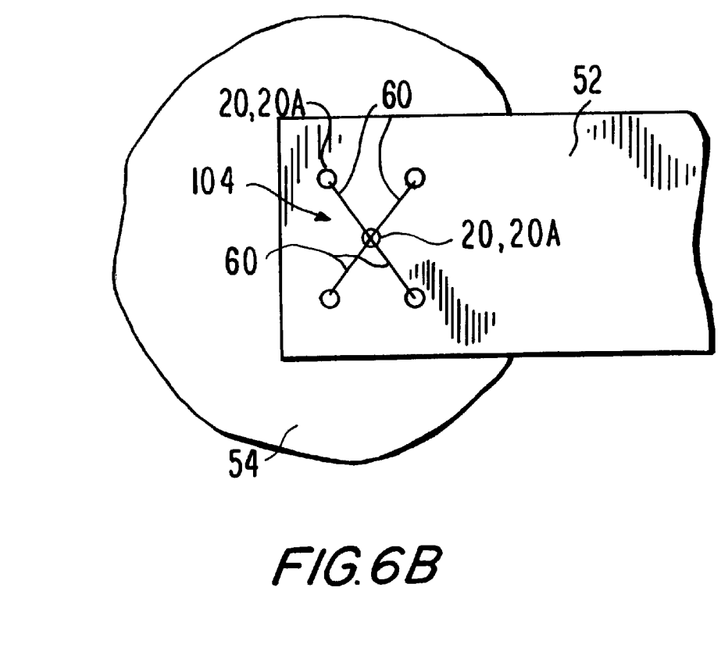
Figures 6C, 7:
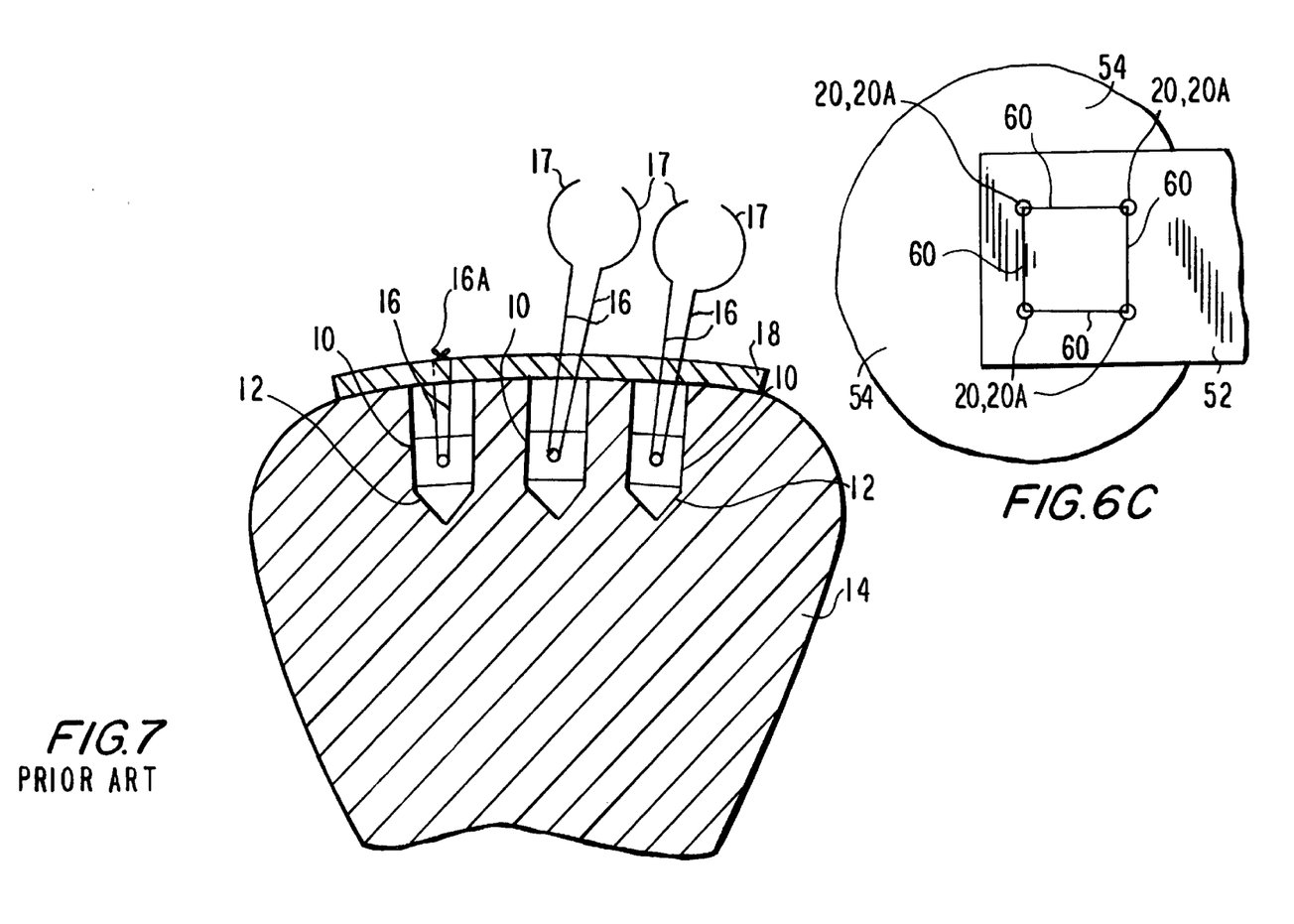
FIG. 7 shows a prior art method of employing suture anchors.

FIGS. 6A, 6B and 6C show examples of arrangements which can be achieved with the surgical fastener assembly according to the present invention. As shown in FIG. 6A, ligament 52 is secured to the bone 54 by a plurality of suture anchors 20, 20A. In FIG. 6A, a surgical fastener assembly comprising a "triple" assembly 100 having three individual suture anchors 20, 20A is shown securing tissue 52 to the tissue 54. Also shown in FIG. 6A is a "double" surgical fastener assembly 102 comprising two suture anchors 20, 20A coupled by a single suture 60 also securing the tissue 52 to the tissue 54.

FIG. 6B shows a "quintuplet" surgical fastener assembly 104 according to the present invention comprising five individual suture anchors connected by sutures 60. As discussed, any number of individual suture anchors 40, 40A can be used coupled together by appropriate lengths of suture 60. Accordingly, the surgical fastener assembly can also comprise a "quadruplet" as shown in FIG. 6C, "sextuplet", (not shown) etc, as necessary. As also discussed, the suture 60 may be a single loop of suture tied together with a single knot 61 or a plurality of lengths of suture tied together with appropriate knots 61 as required. Additionally, as shown in FIG. 6A, combinations of surgical fastener assemblies of various configurations can be employed together.

Figure 8:
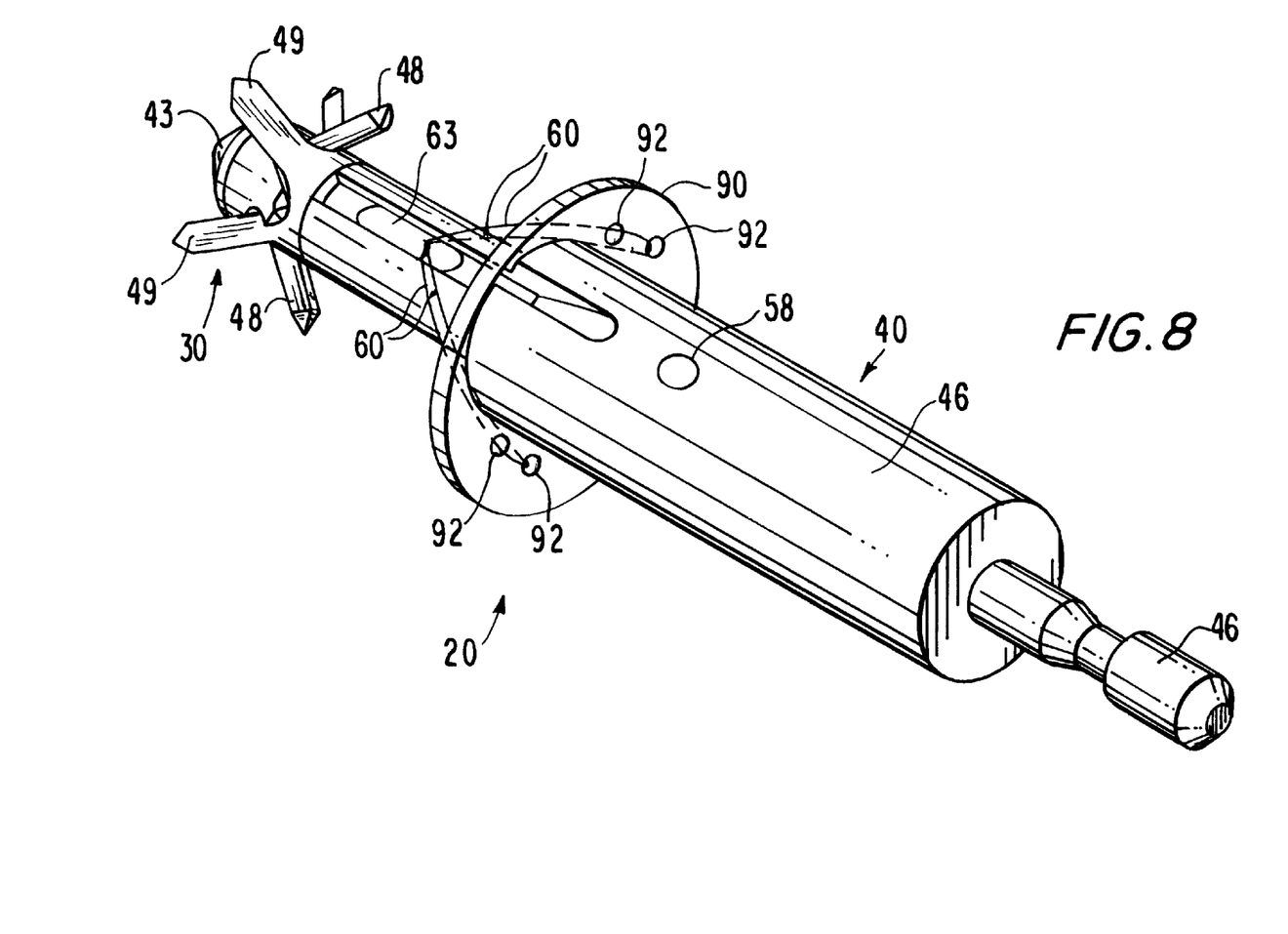
FIG. 8 shows in a perspective view another embodiment of a surgical fastener assembly according to the present invention which includes a single suture anchor employable to secure first and second tissues together.
Figure 9:
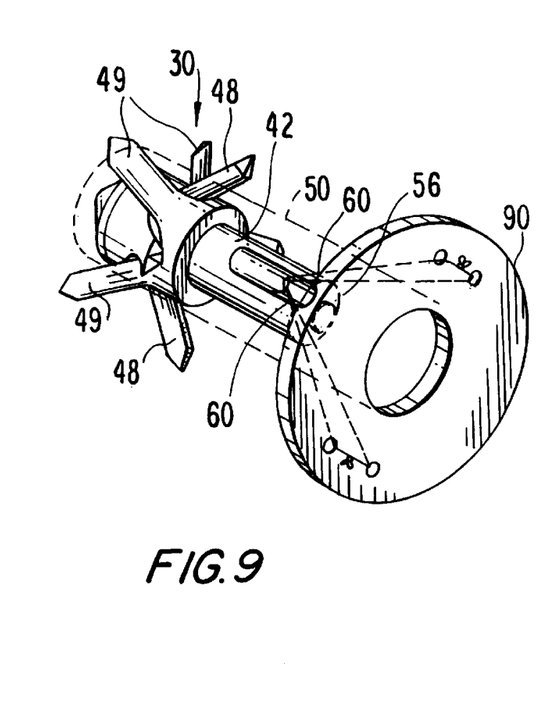
FIG. 9 shows in a perspective view the surgical fastener assembly of FIG. 8 after deployment disposed in a borehole in tissue.
Figure 10:
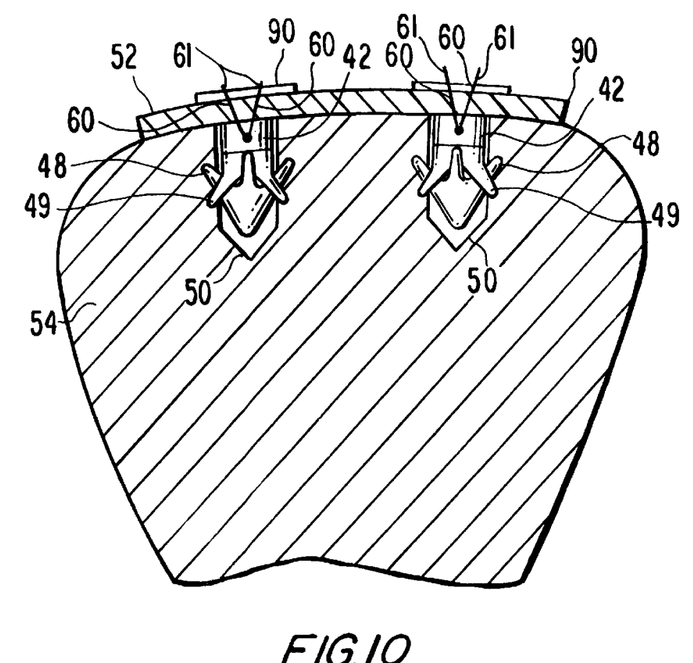
FIG. 10 shows in a side view how the surgical fastener assembly of FIG. 8 may be employed to secure first and second tissues together.

FIGS. 8, 9 and 10 shown an alternative embodiment of the present invention. This embodiment can be employed as a stand-alone surgical fastener assembly which is not be coupled with other individual suture anchors, although a plurality of these assemblies can be used at a single location. In this embodiment, a suture anchor 20 has an extending member, shown as a button element 90, disposed concentrically thereabout proximally of the engaging portion 30 and is fastened by the sutures 60 extending through the suture hole 63 to the engaging portion 30. In FIG. 8, the suture anchor is of the type shown in FIG. 1 having interdigitated longitudinally extending fingers 48 and 49. Alternatively, the embodiment shown in FIGS. 3 and 4 having longitudinally directed fingers extending in only one direction can be used.

The button member 90, which can be disc shaped or have any other shape, such as a square or rectangle, or even comprise a length of wire, for example, forming a T-bar, has a plurality of holes 92 therein through which the sutures are looped. The member 90 should have a width greater than the diameter of the borehole 50. If the member 90 is a bar or a length of wire, the sutures can be wrapped around the wire and the wire should have a length greater than the diameter of the borehole 50. The sutures can be tied off at an appropriate point. A single length of suture can be employed traveling through the hole 63 in the shaft 42 and threading through the holes 92 or individual lengths of suture appropriately tied off may be employed. FIGS. 8 and 9 show the suture anchors 20 in the actuated position. FIG. 9 shows the suture anchor portion 30 which is intended to be secured into the borehole 50 after the shaft 42 has ruptured at the frangible connection 56. As shown in a cross-sectional side view in FIG. 10, the button member 90 has a diameter greater than the diameter of the borehole 50 in the bone 54. The suture anchor of FIGS. 8, 9 and 10 is inserted through an opening in the tissue 52 into the aligned borehole 50. Actuation of the fingers 48 and/or 49 is then caused, so that the fingers 48 and/or 49 penetrate into the sidewall of the borehole. The actuation is made when a suitable tension in the sutures 60 is obtained causing the button member 90 to securely hold the tissue 52 to the tissue 54. upon further actuation, the shaft 42 snaps at the frangible connection 56, leaving the suture anchor in position in the borehole with the button member 90 overlying the tissue 52 and thereby securely holding the tissue 52 in position on the tissue 54. The process is then repeated for additional surgical fastener assemblies, as necessary, to achieve the fixation of tissue 52 to tissue 54.

An advantage of the fastener described is that the member 90, by virtue of its flexible connection to the anchor 20 by sutures, "floats" or pivots on the tissue 52, thus conforming to the surface of the tissue 52. Because the member 90 floats, it is not always the case that the member 90 is perpendicular to the axis of the anchor 20. The member 90 will generally be parallel to the surface of tissue 52, but can be at substantially any angle to the axis of the anchor 20, including perpendicular to the axis and at other angles to the axis. The ability to pivot or "float" is important because this helps to eliminate undue pressure on the tissue 52 surface, distributing the pressure and helping to prevent tissue necrosis due to undue pressure at a particular point or points. This promotes healing.

Although the present invention has been described in relation to particular embodiments thereof, many other variations and modifications and other uses will become apparent to those skilled in the art. Therefore, the present invention should be limited not by the specific disclosure herein, but only by the appended claims.

What is claimed is:

1. A method for fastening a first bio-organic tissue member to a second bio-organic tissue member comprising:

forming a first opening in the first tissue member and an aligned first borehole in the second tissue member;

inserting a first suture anchor, coupled by a suture to a second suture anchor, through the first opening in the first member into the aligned borehole in the second member and securing the first suture anchor in the borehole;

the suture attached to the first suture anchor thereby passing out of the first borehole through the first hole in the first member;

forming a second hole in the first member and an aligned second borehole in the second member;

inserting the second suture anchor through the second opening in the first member into the second borehole in the second member and securing the second suture anchor in the second borehole with a preset tension in the suture connecting the first and second suture anchors together, the suture spanning across a proximal surface of the first member thereby to hold the first member securely to the second member.

2. The method of claim 1, further comprising forming a third opening in the first member and an aligned third borehole in the second member and inserting a third suture anchor coupled by a suture to at least one of the first and second suture anchors through the third opening in the first member into the third borehole in the second member and securing the third suture anchor in the third borehole with a preset tension in the suture connecting the third suture anchor to at least one of the first and second suture anchors, the suture connecting the third suture anchor to at least one of the first and second suture anchors spanning across a proximal surface of the first member thereby to hold the first member securely to the second member.

3. The method of claim 2, further comprising providing an additional suture anchor through a further opening in the first member into an aligned further borehole in the second member and securing the further suture anchor into the further borehole with a preset tension in the suture connecting the further suture anchor to any of the other suture anchors.

4. The method of claim 1, wherein the step of forming the first opening and the first borehole comprises forming the first opening and the first borehole in a single operation.

5. The method of claim 1, wherein the step of forming the second opening in the first member and the second borehole comprises forming the second opening and. second borehole in a single operation.

6. The method of claim 2, wherein the step of forming a third opening in the first member and a third borehole in the second member comprises forming the third opening and third borehole in a single operation.

7. The method of claim 1, wherein the steps of forming the first opening and second opening in the first member comprises using a piercing distal end of the suture anchor to make the first opening and second opening.

8. The method of claim 1, wherein the first opening is made in a separate operation from the first borehole and the second opening is made in a separate operation from the second borehole.

9. The method of claim 1, further comprising providing a plurality of longitudinally extending fingers on each of said suture anchors adapted to move axially to cause the fingers to move against opposed cam surfaces and thereby move radially outwardly to penetrate into a side wall of the borehole to secure the suture anchor in the borehole.

10. The method of claim 1, further comprising providing two sets of longitudinally extending fingers interdigitated with each other on each suture anchor, one set extending proximally and the other set extending distally, and moving the two sets of fingers relatively longitudinally toward each other by the application of a force thereto against respective opposed cam surfaces thereby causing the fingers to move radially outwardly to penetrate into the side wall of the borehole to secure the suture anchor in the borehole.

11. The method of claim 1, further comprising connecting the suture anchors together with a single loop of suture tied together with a single knot.

12. The method of claim 1, further comprising connecting the suture anchors together with a plurality of sutures tied together with appropriate knots.

13. The method of claim 9, further comprising providing a shaft extending concentrically through a cylindrical member of the suture anchor, providing the shaft with two portions connected by a releasable connection, a first portion of the shaft having a hollow member disposed concentrically thereon and bearing said longitudinally directed fingers and a second portion of the shaft having said cylindrical member disposed thereon.

14. The method of claim 13, further comprising providing cam surfaces on the cylindrical member for engaging with the longitudinally directed fingers.

15. The method of claim 14, further comprising providing said releasable connection as a frangible portion of the shaft adapted to rupture at a preset tensile force in the shaft.

16. The method of claim 10, further comprising providing a shaft extending concentrically through a cylindrical member, providing the shaft with two portions connected by a releasable connection, the first portion of the shaft having two hollow members disposed concentrically thereon and each bearing a respective set of said longitudinally directed fingers, the second portion of the shaft having said cylindrical member disposed thereon.

17. The method of claim 16, further comprising providing each hollow member having a respective set of longitudinally directed fingers with cam surfaces disposed thereon between the fingers for causing the fingers of the opposed hollow member to extend outwardly upon application of tensile force in the shaft.

18. The method of claim 16, further comprising providing the releasable connection as a frangible portion of the shaft adapted to rupture at a preset tensile force in the shaft.

19. A method for fastening a first bio-organic tissue member to a second bio-organic tissue member comprising the steps of:

forming a first opening in the first member and an aligned first bore hole in the second member;

inserting an anchor through the first opening in the first member into the aligned first bore hole in the second member and securing the anchor in the first bore hole with an engaging portion of the anchor so that the engaging portion engages and penetrates into walls of the first bore hole, the anchor pivotally connected to an extending member disposed about an axis of the anchor proximally with respect to the engaging portion, the extending member having an extent greater than the diameter of the first bore hole and overlying a portion of a proximal surface of the first member surrounding the first opening; and securing the anchor in the first bore hole with the extending member overlying the proximal surface of the first member with a tension in the pivotal connection between the extending member and the anchor to secure the first member to the second member between the extending member and the second member;

further comprising providing the pivotal connection between the extending member and the anchor as a flexible member.

20. The method of claim 19, further comprising providing the extending member as a disc-shaped planar object.

21. A method for fastening a first bio-organic tissue member to a second bio-organic tissue member comprising the steps of:

forming a first opening in the first member and an aligned first bore hole in the second member;

inserting an anchor through the first opening in the first member into the aligned first bore hole in the second member and securing the anchor in the first bore hole with an engaging portion of the anchor so that the engaging portion engages and penetrates into walls of the first bore hole, the anchor pivotally connected to an extending member disposed about an axis of the anchor proximally with respect to the engaging portion, the extending member having an extent greater than the diameter of the first bore hole and overlying a portion of a proximal surface of the first member surrounding the first opening; and securing the anchor in the first bore hole with the extending member overlying the proximal surface of the first member with a tension in the pivotal connection between the extending member and the anchor to secure the first member to the second member between the extending member and the second member;

further comprising providing the connection between the anchor and the extending member as at least one flexible suture, thereby providing a floating flexible connection between the extending member and the anchor.

22. A method for fastening a first bio-organic tissue member to a second bio-organic tissue member comprising the steps of:

forming a first opening in the first member and an aligned first bore hole in the second member;

inserting an anchor through the first opening in the first member into the aligned first bore hole in the second member and securing the anchor in the first bore hole with an engaging portion of the anchor so that the engaging portion engages and penetrates into walls of the first bore hole, the anchor pivotally connected to an extending member disposed about an axis of the anchor proximally with respect to the engaging portion, the extending member having an extent greater than the diameter of the first bore hole and overlying a portion of a proximal surface of the first member surrounding the first opening; and securing the anchor in the first bore hole with the extending member overlying the proximal surface of the first member with a tension in the pivotal connection between the extending member and the anchor to secure the first member to the second member between the extending member and the second member;

further comprising providing a plurality of holes in the extending member for receiving a plurality of suture lengths coupling the extending member to the anchor.

23. A method for fastening a first bio-organic tissue member to a second bio-organic tissue member comprising the steps of:

forming a first opening in the first member and an aligned first bore hole in the second member;

inserting an anchor through the first opening in the first member into the aligned first bore hole in the second member and securing the anchor in the first bore hole with an engaging portion of the anchor so that the engaging portion engages and penetrates into walls of the first bore hole, the anchor pivotally connected to an extending member disposed about an axis of the anchor proximally with respect to the engaging portion, the extending member having an extent greater than the diameter of the first bore hole and overlying a portion of a proximal surface of the first member surrounding the first opening; and securing the anchor in the first bore hole with the extending member overlying the proximal surface of the first member with a tension in the pivotal connection between the extending member and the anchor to secure the first member to the second member between the extending member and the second member;

further comprising providing the connection between the anchor and the extending member as a plurality of sutures, thereby providing a floating connection between the extending member and the anchor.

24. The method of claim 19, further comprising providing a plurality of longitudinally extending fingers on the anchor adapted to move axially to cause the fingers to move against opposed cam surfaces and thereby move radially outwardly to penetrate into a side wall of the borehole to secure the anchor in the first borehole.

25. A method for fastening a first bio-organic tissue member to a second bio-organic tissue member comprising the steps of:

forming a first opening in the first member and an aligned first bore hole in the second member;

inserting an anchor through the first opening in the first member into the aligned first bore hole in the second member and securing the anchor in the first bore hole with an engaging portion of the anchor so that the engaging portion engages walls of the first bore hole, the anchor pivotally connected to an extending member disposed about an axis of the anchor proximally with respect to the engaging portion, the extending member having an extent greater than the diameter of the first bore hole and overlying a portion of a proximal surface of the first member surrounding the first opening; and securing the anchor in the first bore hole with the extending member overlying the proximal surface of the first member with a preset tension in the pivotal connection between the extending member and the anchor to secure the first member to the second member between the extending member and the second member;

further comprising providing two sets of longitudinally extending fingers interdigitated with each other on the anchor, one set extending proximally and the other set extending distally, the two sets of fingers moving relatively toward each other upon application of a force thereto against respective cam surfaces thereby causing the fingers to move radially outwardly to penetrate into the side wall of the borehole to secure the anchor in the borehole.

26. A method for fastening a first bio-organic tissue member to a second bio-organic tissue member comprising the steps of:

forming a first opening in the first member and an aligned first bore hole in the second member;

inserting an anchor through the first opening in the first member into the aligned first bore hole in the second member and securing the anchor in the first bore hole with an engaging portion of the anchor so that the engaging portion engages and penetrates into walls of the first bore hole, the anchor pivotally connected to an extending member disposed about an axis of the anchor proximally with respect to the engaging portion, the extending member having an extent greater than the diameter of the first bore hole and overlying a portion of a proximal surface of the first member surrounding the first opening; and securing the anchor in the first bore hole with the extending member overlying the proximal surface of the first member with a tension in the pivotal connection between the extending member and the anchor to secure the first member to the second member between the extending member and the second member;

further comprising connecting the anchor to the extending member with a single loop of suture tied with a single knot.

27. A method for fastening a first bio-organic tissue member to a second bio-orzanic tissue member comprising the steps of:

forming a first opening in the first member and an aligned first bore hole in the second member;

inserting an anchor through the first opening in the first member into the aligned first bore hole in the second member and securing the anchor in the first bore hole with an engaging portion of the anchor so that the engaging portion engages and penetrates into walls of the first bore hole, the anchor pivotally connected to an extending member disposed about an axis of the anchor proximally with respect to the engaging portion, the extending member having an extent greater than the diameter of the first bore hole and overlying a portion of a proximal surface of the first member surrounding the first opening, and securing the anchor in the first bore hole with the extending member overlying the proximal surface of the first member with a tension in the pivotal connection between the extending member and the anchor to secure the first member to the second member between the extending member and the second member;

further comprising connecting the anchor to the extending member with a plurality of sutures tied together with appropriate knots.

28. A method for fastening a first bio-organic tissue member to a second bio-organic tissue member comprising the steps of:

forming a first opening in the first member and an aligned first bore hole in the second member;

inserting an anchor through the first opening in the first member into the aligned first bore hole in the second member and securing the anchor in the first bore hole with an engaging portion of the anchor so that the engaging portion engages and penetrates into walls of the first bore hole, the anchor pivotally connected to an extending member disposed about an axis of the anchor proximally with respect to the engaging portion, the extending member having an extent greater than the diameter of the first bore hole and overlying a portion of a proximal surface of the first member surrounding the first opening; and securing the anchor in the first bore hole with the extending member overlying the proximal surface of the first member with a tension in the pivotal connection between the extending member and the anchor to secure the first member to the second member between the extending member and the second member;

further comprising providing a plurality of longitudinally extending fingers on the anchor adapted to move axially to cause the fingers to move against opposed cam surfaces and thereby move radially outwardly to penetrate into a side wall of the borehole to secure the anchor in the first borehole and;

further comprising providing the anchor with a shaft extending concentrically through a cylindrical member, the shaft comprising two portions connected by a releasable connection, a first portion of the shaft having a hollow member disposed concentrically thereon and bearing said longitudinally directed fingers, the second portion of the shaft having said cylindrical member disposed thereon.

29. A method for fastening a first bio-organic tissue member to a second bio-organic tissue member comprising the steps of:

forming a first opening in the first member and an aligned first bore hole in the second member;

inserting an anchor through the first opening in the first member into the aligned first bore hole in the second member and securing the anchor in the first bore hole with an engaging portion of the anchor so that the engaging portion engages and penetrates into walls of the first bore hole, the anchor pivotally connected to an extending member disposed about an axis of the anchor proximally with respect to the engaging portion, the extending member having an extent greater than the diameter of the first bore hole and overlying a portion of a proximal surface of the first member surrounding the first opening; and securing the anchor in the first bore hole with the extending member overlying the proximal surface of the first member with a tension in the pivotal connection between the extending member and the anchor to secure the first member to the second member between the extending member and the second member;

further comprising forming the first opening in the first member and the first borehole in a single operation.

30. A method for fastening a first bio-organic tissue member to a second bio-organic tissue member comprising the steps of:

forming a first opening in the first member and an aligned first bore hole in the second member;

inserting an anchor through the first opening in the first member into the aligned first bore hole in the second member and securing the anchor in the first bore hole with an engaging portion of the anchor so that the engaging portion engages and penetrates into walls of the first bore hole, the anchor pivotally connected to an extending member disposed about an axis of the anchor proximally with respect to the engaging portion, the extending member having an extent greater than the diameter of the first bore hole and overlying a portion of a proximal surface of the first member surrounding the first opening; and securing the anchor in the first bore hole with the extending member overlying the proximal surface of the first member with a tension in the pivotal connection between the extending member and the anchor to secure the first member to the second member between the extending member and the second member;

further comprising forming the first opening in the first member and the first borehole in separate operations.

31. A method for fastening a first bio-organic tissue member to a second bio-organic tissue member comprising the steps of:

forming a first opening in the first member and an aligned first bore hole in the second member;

inserting an anchor through the first opening in the first member into the aligned first bore hole in the second member and securing the anchor in the first bore hole with an engaging portion of the anchor pivotally connected to an extending member disposed about an axis of the anchor proximally with respect to the engaging portion, the extending member having an extent greater than the diameter of the first bore hole and overlying a portion of a proximal surface of the first member surrounding the first opening; and securing the anchor in the first bore hole with the extending member overlying the proximal surface of the first member with a preset tension in the pivotal connection between the extending member and the anchor to secure the first member to the second member between the extending member and the second member, further comprising the steps of:

forming a second opening in the first member and an aligned second bore hole in the second member;

inserting a second anchor through the second opening in the first member into the aligned second bore hole in the second member and securing the second anchor in the second bore hole with an engaging portion of the second anchor, the second anchor connected to a second extending member disposed about an axis of the second anchor proximally with respect to the engaging portion of the second anchor, the second extending member having an extent greater than the diameter of the second bore hole and overlying a portion of a proximal surface of the first member surrounding the second opening; and securing the second anchor in the second bore hole with the second extending member overlying the proximal surface of the first member with a preset tension in the pivoted connection between the second extending member and the second anchor to secure further the first member to the second member between the second extending member and the second member.

32. The method of claim 31, wherein the pivotal connection between the second extending member and the second anchor comprises at least one suture thereby providing a floating connection between the extending member and the anchor.

33. The method of claim 28, further comprising providing the releasable connection as a frangible portion of the shaft adapted to rupture at a preset tensile force in the shaft.

34. The method of claim 25, further comprising providing the anchor with a shaft extending concentrically through a cylindrical member, providing the shaft with a releasable connection connecting two portions of the shaft together, a first portion of the shaft having two hollow members disposed concentrically thereon and each bearing a respective set of said longitudinally directed fingers, a second portion of the shaft having said cylindrical member disposed thereon.

35. The method of claim 34, further comprising providing the releasable connection as a frangible portion of the shaft adapted to rupture at a preset tensile force in the shaft.

* * * * *